United States Patent [19]

Monroe

[11] 4,380,537

[45] Apr. 19, 1983

[54] STABILIZED INSECTICIDE FORMULATIONS

[75] Inventor: Roger F. Monroe, Midland, Mich.

[73] Assignee: The Dow Chemical Company, Midland, Mich.

[21] Appl. No.: 954,258

[22] Filed: Oct. 24, 1978

Related U.S. Application Data

[63] Continuation-in-part of Ser. No. 935,421, Aug. 21, 1978, abandoned, which is a continuation-in-part of Ser. No. 853,779, Nov. 21, 1977, abandoned.

[51] Int. Cl.$^3$ .................... A01N 57/00; A01N 57/26
[52] U.S. Cl. .................... 424/200; 424/213; 424/216; 424/217; 424/218; 424/220; 424/225
[58] Field of Search ............ 424/200, 225, 279, 213, 424/216, 217, 218, 220

[56] References Cited

U.S. PATENT DOCUMENTS

| | | | |
|---|---|---|---|
| 2,599,516 | 6/1952 | Moyle | 260/964 |
| 2,929,762 | 3/1960 | Wasco et al. | 260/959 |
| 3,062,709 | 11/1962 | Ordas | 424/213 |
| 3,086,907 | 4/1963 | Hessel | 424/279 |
| 3,089,807 | 5/1963 | Trademan et al. | 71/71 |
| 3,155,568 | 11/1964 | Surgant et al. | 424/175 |
| 3,235,368 | 2/1966 | Surgant | 71/217 |
| 3,244,586 | 4/1966 | Rigterink | 424/200 |
| 3,284,295 | 11/1966 | Johnson | 424/218 |
| 3,700,694 | 10/1972 | Siddall | 424/279 |
| 3,923,997 | 12/1975 | Meuly | 424/279 |

FOREIGN PATENT DOCUMENTS 1052552  12/1966  United Kingdom .

OTHER PUBLICATIONS

King's Chemical Evaluated as Insecticides and Repellents at Orlando, Fla., May 1954, pp. 1-17, 98 & 99.
Harvey et al., Pesticidal Formulation Research Advances in Chemistry, Series 86, pp. 81-90, (1969).

*Primary Examiner*—Allen J. Robinson
*Attorney, Agent, or Firm*—S. Preston Jones; Ronald G. Brookens

[57] ABSTRACT

Insecticide formulations containing an organophosphorus insecticide on clay carriers are stabilized by incorporating from about 0.5 to about 10 weight percent of a lactone in said formulation.

10 Claims, No Drawings

STABILIZED INSECTICIDE FORMULATIONS

CROSS-REFERENCE TO RELATED APPLICATION

This is a continuation-in-part of application Ser. No. 935,421, filed Aug. 21, 1978 now abandoned which is in turn a continuation-in-part of application Ser. No. 853,779, filed Nov. 21, 1977 now abandoned.

PRIOR ART

The preparation of stabilized solid pesticide formulations is the subject of many patents in the prior art. For example, in U.S. Pat. No. 3,062,709, dimethyl sulfoxide is employed as a stabilizer. In U.S. Pat. No. 3,284,295 amides and thioamides of alkanoic acids are employed as stabilizers. In U.S. Pat. No. 3,235,368, aliphatic and cycloaliphatic alcohols act as stabilizers. British Pat. No. 1,052,552 teaches the use of glycol monoethyl ether or thioether as stabilizers. Pesticidal Formulations Research, Advances in Chemistry, Series 86, Harvey et al. "The Decomposition of Guthion in N-methyl-2-pyrrolidone and Butyrolactone", pages 81-90 (1969) American Chemical Society, is directed to a comparison of the chemical stability of Guthion in two solvent systems.

BACKGROUND OF THE INVENTION

To permit effective application of many pesticides by airborne or ground spreading equipment, the active pesticide is impregnated on a solid carrier material which may be diluted to field strength prior to application. The physical properties of the solid formulation, such as ease of flow and retention on the plant, are of the essence. Clays are frequently preferred as the carrier material because of the desirable physical properties of solid pesticide formulation which are based on clay carriers. Some of the clay materials that have been found to be especially suitable as carriers for organic pesticides are the attapulgite and montmorillonite clays. The calcined clays have been considered to possess excellent physical properties as carrier material for organic toxicants. Although the above clays possess excellent flow properties after impregnation with organic toxicants and are readily amenable to impregnation with organic toxicants, the calcined clays unfortunately tend to cause certain types of toxicants, such as thiophosphate ester toxicants, to decompose chemically and to lose their potency when the solid toxicant compositions are stored for long periods in temperate climates or for shorter periods in the tropics. Improvements in stabilizing the clay formulations are continuously being sought.

SUMMARY OF THE INVENTION

The present invention provides a stabilized insecticidal composition comprising an organic phosphate toxicant, a solid carrier therefor having a tendency to decompose said phosphate, and a lactone as stabilizer therefor.

One object of this invention is to increase the active life of insect toxicants and to provide a means for more effective insect control. A further object is to provide for prolonged activity of the insecticide during storage and to enable a more uniform reproducible control of insects.

For several years it has increasingly become the practice to put active insecticides onto solid carriers, especially those which are in granulated form. Because of the use of solid carriers, instead of liquid carriers, it is possible to save work, such as preparation immediately before use, and in some cases additional mixing of spraying liquids as well as the undesirable transportation of large quantities of water. In addition, less expensive carriers are normally employed for solid formulations.

Typically, a granular formulation may contain from about 2 percent to about 40 percent of the active insecticide by weight. This type of formulation is generally used as such without further dilution.

The toxicant ingredients which are stabilized by the present invention are in the phosphorus containing insecticides.

Phosphorus compounds useable with the present invention include compounds selected from the class of halopyridyl phosphates set forth in U.S. Pat. No. 3,244,586 which are of the formula 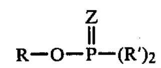 wherein R represents halopyridyl, Z represents oxygen or sulfur and each R′ represents loweralkoxy of 1 to 8 carbon atoms, amino or loweralkylamino of 1 to 8 carbon atoms.

Additionally, phosphoramidates set forth in U.S. Pat. No. 2,929,762 which are of the formula 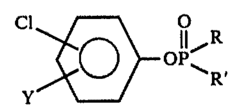 wherein Y represents alkyl of 1 to 5 carbon atoms, R represents alkyl of 1 to 4 carbon atoms and R′ represents amino or alkylamino of 1 to 4 carbon atoms.

Also included are compounds taught in U.S. Pat. No. 2,599,516 which are of the formula wherein R is methyl or ethyl.

Additional examples of phosphorus compounds which can be stabilized according to the present invention are Di-Syston [O,O-diethyl-S-(ethylthio)ethyl phosphorodithioate], Systox [O,O-diethyl O (and S)-2-(ethylthio)ethyl phosphorothioates], Thimet [O,O-diethyl (S-ethylmercapto)methyl dithiophosphate], Malathion [S-(1,2-dicarboethoxyethyl) O,O-dimethyl dithiophosphate], Meta-Systox-R [O,O-dimethyl-S-2(ethylsulfinyl)ethyl phosphorothiate], Ekatin [O,O-dimethyl S-2(ethylthio) ethyl phosphorothioate], Bayer 23655 [O,O-dimethyl S-2-(ethylsulfinyl)isopropyl phosphorothioate], Bayer S-299 [O,O-dimethyl-S-2(ethylsulfinyl)ethyl phosphorodithioate], Bayer 29493 [O,O-dimethyl-O-(4-methylthio)m-tolyl phosphorothioate], Meta-Systox-I [O,O-dimethyl S-2(ethylthio)ethyl phosphorothioate], Parathion [O,O-diethyl-O-p-nitrophenyl phosphorothioate], Methyl Parathion (O,O-dimethyl-O-p-nitrophenyl phosphorothioate), S-tertiary butylmercaptomethyl O,O-diethyl dithiophosphate, S-secondary amyl mercaptomethyl O,O-diethyl dithiophosphate, S-n-butoxymethyl O,O-bis (2-chloroethyl) dithiophosphate, S-tertiary butylmercaptomethyl O,O-bis(2-chloroethyl)dithiophosphate, counter [S-[[(1,1-dimethylethyl)thio]methyl]-O,O-diethylphosphorodithioate], Bromophos [O-(4-bromo-2,5-dichlorophenyl)-O,O-dimethylphosphorothioate], Merck CMS 2957 [O,O-diethyl-O-2,4-dichloro-5-(methylthio)phenyl thionophosphate] and other such phosphorus compounds.

The carriers or diluents generally used with these insect toxicants, and which are active in deteriorating the active toxicants, set forth above, when mixed therewith, are solids of the class consisting of kaolin clays such as Kaolinite, dickite, nacrite, anauxite, halloysite, endellite and barden clay; montmorillonite clays such as beidellite, nontromite, montmorillonite, hectorite, saponite, savconite and bentonite; attapulgites such as fuller's earth, attapulgite and sepiolite; diatomaceous earths such as diatomite and kieselguhr and vermiculite such as biotite and synthetic silicates such as Micro-cel and Silene EF, various talc.

While the solid carriers above discussed are very useful in formulating the herein defined toxicants for reasons of their inexpensiveness, availability, ease of handling, absorbency characteristics, durability, and other desirable physical properties, they have the disadvantageous property, to varying degrees, of degrading or decomposing the insect toxicant when intimately mixed therewith. This degradation process is significant and troublesome since dry formulations are often prepared as concentrates or even field strength materials and then stored for periods which may be as long as a year or more. During this storage period, the effect of the carrier or diluent on the insect toxicant ingredient may reduce its effectiveness to the point where satisfactory insect control under field conditions is no longer obtainable.

The nature of the reaction or effect of the carriers on the insecticide has never been fully elucidated. The rate of toxicant deterioration may vary by the action of different carriers or diluents.

To solve the present problem, it has been found necessary to neutralize the activity of the solid carriers and diluents so that they are inert to the insect toxicant and will allow protracted storage of dry insecticide formulations without deterioration of insecticidal activity of such formulation.

Since the formulations herein concerned are used preponderantly in agriculture, any treatment of the carriers and diluents used must necessarily not render the formulation unfit for agricultural use on food and forage crops at time of harvest. Thus, the treatment must not render the formulation phytotoxic. The treatment must likewise not be hazardous from a warm-blooded animal toxicity standpoint, or otherwise increase the hazard in the utilization of insecticide formulations. Also, of primary importance, and considering the economics involved, the treatment must not involve expensive materials, nor can the process of treatment be complex. Another consideration in the present problem is that the treatment must not affect the insecticidal activity of the toxicant employed.

It has now been found that the solid carriers and diluents which were previously described and which are active in deteriorating the classes of insecticides herein concerned can be made substantially inert by the addition of a small amount of a lactone.

Lactones useful in preventing or reducing deterioration include, for example, butyrolactone, 2-acetyl-γ-butyrolactone, γ-valerolactone, δ-valerolactone, γ-octanoiclactone and ε-caprolactone. These lactones are all well known and can be obtained commercially.

Lactones have the beneficial effect of alleviating or eliminating degradation or deterioration of the insect toxicant ingredient in dry insecticide formulations when contained in such formulation in amounts varying between about 0.5 percent to about 10 percent by weight based on the weight of the carrier and toxicant contained in the formulation. A preferred concentration of the lactone to dry insecticide formulation is about 2 percent to about 4 percent by weight of the ultimate formulation.

The art of blending materials with solid carriers and diluents of the class described is well known, and the liquid lactone additives employed in the present invention can be blended with these solid materials by any known means. For example, the use of commercial type mixers or blenders is adequate. The lactone can be added to and blended with the solid carriers either alone or in combination with an inert, relatively volatile solvent which can be removed after blending. The lactone can be added to and blended with the solid carriers prior to blending the insect toxicant therewith.

In the alternative, the lactone can be added to the solid carriers during the same blending operation wherein mixing of the insect toxicant and carrier is achieved.

It is preferred to dissolve the toxicant in the lactone and to blend this mixture with the solid carrier. By employing this preferred blending technique a saving is achieved in that only one blending step is needed.

In addition, it has been found that the use of lactones as stabilizers overcomes the caking problem associated with many stabilizers in that product does not cake but is rather a free flowing material and allows for a more marketable product.

DESCRIPTION OF SOME PREFERRED EMBODIMENTS

The following examples serve to illustrate the practice of the present invention but are not intended to be limitations upon the overall scope of the same.

EXAMPLE I

Formulations containing about 15 percent chlorpyrifos[O,O-diethyl O-(3,5,6-trichloro-2-pyridyl)phosphorothioate] and from 0 to 4 percent by weight of the ultimate composition of butyrolactone and one of the hereinafter set forth clays were prepared and held under accelerated storage conditions at a temperature of 125° F. for up to 70 days. At 0 day, 14 days (equal to 1 year of storage at room temperature), 30 days (equal to 2 years of storage at room temperature) and 70 days (equal to 3 years of storage at room temperature) after storage, the formulations were analyzed to determine the percentage of the active phosphate compound remaining and the percent pyridinol present (a decomposition product formed during storage). The results of these analyses are set forth below in Table I.

TABLE I

| Clay Carrier | Percent Butyro-lactone In For-mulation | Percent Chlorpyrifos Remaining In Formulation After Indicated Days In Storage at 125° F. | | | | Percent Pyridinol Formed In Formulation After Indicated Days In Storage at 125° F. | | | |
|---|---|---|---|---|---|---|---|---|---|
| | | 0 | 14 | 30 | 70 | 0 | 14 | 30 | 70 |
| Attapulgus - 25/50 LVM | 4 | 100 | 88 | 85 | 83 | 0.08 | 0.66 | 0.96 | 1.46 |
| (A calcined attapulgus clay by | 2 | 100 | 86 | 78 | 71 | 0.33 | 1.16 | 1.42 | 2.02 |
| Engelhard Co.) | 1 | 100 | 87 | 78 | 73 | 0.22 | 1.53 | 1.78 | 2.52 |
| | 0 | 100 | 85 | 74 | 73 | 0.33 | 1.70 | 1.89 | 2.64 |
| Agsob - 24/48 | 4 | 100 | 96 | 91 | 89 | 0.05 | 0.41 | 0.36 | 0.93 |
| (A calcined attapulgus clay by | 2 | 100 | 96 | 86 | 83 | 0.10 | 0.70 | 0.80 | 1.41 |
| Oil-Dri Co.) | 0 | 100 | 85 | 82 | 77 | 0.30 | 1.45 | 1.71 | 1.02 |
| Montmorillonite - 8/16 LVM | 4 | 100 | 96 | 94 | 99 | 0.07 | 0.29 | 0.37 | 0.72 |
| (A calcined montmorillonite clay | 2 | 100 | 100 | 94 | 97 | 0.14 | 0.40 | 0.62 | 0.99 |
| by Oil-Dri Co.) | 0 | 100 | 100 | 97 | 88 | 0.36 | 1.15 | 0.50 | 2.19 |
| Montmorillonite - 24/48 LVM | 4 | 100 | 100 | 94 | — | 0.0 | 0.18 | 0.58 | — |
| (A calcined montmorillonite clay | 2 | 100 | 100 | 95 | — | 0.0 | 0.33 | 0.93 | — |
| by Oil-Dri Co.) | 0 | 100 | 99 | 86 | — | 0.0 | 0.71 | 2.19 | — |
| Creek-O-Nite | 4 | 100 | 99 | 96 | 99 | 0.0 | 0.14 | 0.23 | 0.40 |
| (A calcined montmorillonite clay | 3 | 100 | 97 | 95 | 93 | 0.0 | 0.14 | 0.26 | 0.46 |
| by Lowes, Inc.) | 2 | 100 | 92 | 90 | 93 | 0.0 | 0.18 | 0.38 | 0.54 |
| | 1 | 100 | 95 | 90 | 92 | 0.0 | 0.28 | 0.49 | 0.75 |
| | 0 | 100 | 83 | 83 | 80 | 0.11 | 0.98 | 1.34 | 0.78 |

EXAMPLE II

Formulations containing about 15 percent chlorpyrifos[O,O-diethyl O-(3,5,6-trichloro-2-pyridyl)phosphorothioate] and from 0 to 4 percent by weight of the ultimate composition of butyrolactone and montmorillonite clay were prepared and held under accelerated storage conditions at a temperature of 125° F. for up to 70 days. At 0 day, 14 days (equal to 1 year of storage at room temperature), 30 days (equal to 2 years of storage at room temperature) and 70 days (equal to 3 years of storage at room temperature) after storage, the formulations were analyzed to determine the percentage of the active phosphate compound remaining and the percent pyridinol present (a decomposition product formed during storage). The results of these analyses are set forth below in Table II.

EXAMPLE III

Formulations containing about 15 percent chlorpyrifos-methyl[O,O-dimethyl O-(3,5,6-trichloro-2-pyridyl)phosphorothioate] and from 0 to 4 percent by weight of the ultimate composition of butyrolactone and montmorillonite clay were prepared and held under accelerated storage conditions at a temperature of 125° F. for up to 30 days. At 0 day, 14 days (equal to 1 year of storage at room temperature) and 30 days (equal to 2 years of storage at room temperature) after storage, the formulations were analyzed to determine the percentage of the active phosphate compound remaining and the percent pyridinol present (a decomposition product formed during storage). The results of these analyses are set forth below in Table III.

TABLE II

| Clay Carrier | Percent Butyro-lactone In For-mulation | Percent Chlorpyrifos Remaining In Formulation After Indicated Days In Storage at 125° F. | | | | Percent Pyridinol Formed In Formulation After Indicated Days In Storage at 125° F. | | | |
|---|---|---|---|---|---|---|---|---|---|
| | | 0 | 14 | 30 | 70 | 0 | 14 | 30 | 70 |
| Creek-O-Nite | 4 | 100 | 99 | 100 | 99 | 0.0 | 0.15 | 0.21 | 0.29 |
| (A calcined montmorillonite clay | 3 | 100 | 92 | 99 | 92 | 0.0 | 0.17 | 0.25 | 0.39 |
| by Lowes, Inc.) | 2 | 100 | 97 | 99 | 96 | 0.0 | 0.19 | 0.29 | 0.50 |
| | 1 | 100 | 96 | 92 | 94 | 0.0 | 0.38 | 0.62 | 0.91 |
| | 0 | 100 | 83 | 82 | 80 | 0.11 | 0.98 | 1.34 | 1.78 |

TABLE III

| Clay Carrier | Percent Butyro-lactone In For-mulation | Percent Chlorpyrifos Remaining In Formulation After Indicated Days In Storage at 125° F. | | | Percent Pyridinol Formed In Formulation After Indicated Days In Storage at 125° F. | | |
|---|---|---|---|---|---|---|---|
| | | 0 | 14 | 30 | 0 | 14 | 30 |
| Creek-O-Nite | 4 | 100 | 96 | 94 | 0.0 | 0.62 | 0.96 |
| (A calcined montmorillonite clay | 3 | 100 | 94 | 92 | 0.0 | 0.75 | 1.15 |
| by Lowes, Inc.) | 2 | 100 | 96 | 82 | 0.0 | 0.93 | 1.32 |
| | 1 | 100 | 93 | 83 | 0.0 | 1.20 | 1.70 |
| | 0 | 100 | 83 | 69 | 0.11 | 1.73 | 2.83 |

EXAMPLE IV

Formulations containing about 15 percent ronnel [O,O-dimethyl O-(2,4,5-trichlorophenyl)phosphorothioate] and from 0 to 4 percent by weight of the ultimate composition of butyrolactone and montmorillonite clay were prepared and held under accelerated storage conditions at a temperature of 125° F. for up to 30 days. At 0 day, 14 days (equal to 1 year of storage at room temperature) and 30 days (equal to 2 years of storage at room temperature) after storage, the formulations were analyzed to determine the percentage of the active phosphate compound remaining. The results of these analyses are set forth below in Table IV.

TABLE IV

| Clay Carrier | Percent Butyrolactone In Formulation | Percent Chlorpyrifos Remaining In Formulation After Indicated Days In Storage at 125° F. | | |
|---|---|---|---|---|
| | | 0 | 14 | 30 |
| Creek-O-Nite | 4 | 100 | 100 | 99 |
| (A calcined montmorillonite clay | 3 | 100 | 100 | 100 |
| by Lowes, Inc.) | 2 | 100 | 100 | 97 |
| | 1 | 100 | 100 | 94 |
| | 0 | 100 | 70 | 71 |

EXAMPLE V

Formulations containing ~14.2 percent ronnel [O,O-dimethyl O-(2,4,5-trichlorophenyl)phosphorothioate] and 0 and 4 percent by weight of one of the hereinafter set forth lactones and montmorillonite clay were prepared and held under accelerated storage conditions at a temperature of 122° F. for up to 60 days. At 0 days, 14 days (equal to ~1 year of storage at room temperature), 30 days (equal to 2 years of storage at room temperature) and 60 days (equal to ~3 years of storage at room temperature) after storage, the formulations were analyzed to determine the percentage of the active phosphate compound remaining. The results of these analyses are set forth below in Table V.

TABLE V

| Clay Carrier | Lactone Employed | Percent Lactone In Formulation | Percent Ronnel Remaining In Formulation After Indicated Days In Storage at 122° F. | | | |
|---|---|---|---|---|---|---|
| | | | 0 | 14 | 30 | 60 |
| A6-Sorb 24/48 MB Clay | δ-valerolactone | 4 | 100 | 95.5 | 89.7 | 85.3 |
| (A calcined montmorillonite clay by Oil-Dri | γ-valerolactone | 4 | 100 | 100 | 93.2 | 89.1 |
| nite clay by Oil-Dri | γ-octanoiclactone | 4 | 100 | 97.9 | 89.1 | 88.4 |
| Corporation) | ε-caprolactone | 4 | 100 | 94.2 | 90.4 | 86.5 |
| | 2-acetyl-γ-butyrolactone | 4 | 100 | 100 | 97.3 | 92.5 |
| Control | — | — | 100 | 67.5 | 62.8 | 49.6(a) |

(a)Sample analysed after 70 days.

What is claimed is:

1. In a solid stabilized insecticidal composition mixture which comprises from about 2 to about 40 percent by weight of an organophosphorous insecticide, a solid granular clay carrier therefor, which carrier causes deterioration of said organophosphorous insecticide mixed therewith, and a stabilizing amount of a stabilizer for said mixture, the improvement in said composition which comprises using as the stabilizer, from about 0.5 to about 10% by weight of the ultimate composition of a lactone selected from the group consisting of butyrolactone, δ-valerolactone, γ-valerolactone, γ-octanoiclactone, ε-caprolactone and 2-acetyl-γ-butyrolactone.

2. The stabilized insecticidal composition as defined in claim 1 wherein the solid clay carrier is a montmorillonite clay or an attapulytic clay.

3. The stabilized insecticidal composition as defined in claim 2 wherein the lactone stabilizer is present in an amount of from about 2 to about 4 percent by weight of the ultimate composition.

4. The stabilized insecticidal composition as defined in claim 3 wherein the organophosphorous insecticide is O,O-diethyl O-(3,5,6-trichloro-2-pyridinyl)phosphorothioate, O,O-dimethyl O-(3,5,6-trichloro-2-pyridinyl)phosphorothioate or O,O-dimethyl O-(2,4,5-trichlorophenyl)phosphorothioate.

5. The stabilized insecticidal composition as defined in claim 4 wherein the lactone stabilizer is butyrolactone.

6. The stabilized insecticidal composition as defined inclaim 4 wherein the lactone stabilizer is δ-valerolactone.

7. The stabilized insecticidal composition as defined in claim 4 wherein the lactone stabilizer is γ-valerolactone.

8. The stabilized insecticidal composition as defined in claim 4 wherein the lactone stabilizer is γ-octanoiclactone.

9. The stabilized insecticidal composition as defined in claim 4 wherein the lactone stabilizer is ε-caprolactone.

10. The stabilized insecticidal composition as defined in claim 4 wherein the lactone stabilizer is 2-acetyl-γ-butyrolactone.

* * * * *